United States Patent [19]

Yabuta et al.

[11] Patent Number: 5,504,242
[45] Date of Patent: Apr. 2, 1996

[54] ACYL CARBAMATE CONTAINING A HYDROXYL GROUP AND PROCESS FOR PRODUCING THE SAME

[75] Inventors: Masami Yabuta, Katano; Satoshi Urano, Tsuzuki, both of Japan

[73] Assignee: Nippon Paint Co., Ltd., Osaka, Japan

[21] Appl. No.: 437,128

[22] Filed: May 5, 1995

[30] Foreign Application Priority Data

May 6, 1994 [JP] Japan .................................. 6-094399

[51] Int. Cl.⁶ .................................................. C07C 271/02
[52] U.S. Cl. ........................... 560/32; 560/157; 560/162; 560/163; 560/166
[58] Field of Search .............................. 560/29, 160, 32, 560/157, 162, 163, 166

[56] References Cited

U.S. PATENT DOCUMENTS 4,602,033  7/1986  Heywang et al. ...................... 560/32

Primary Examiner—José G. Dees
Assistant Examiner—Joseph M. Conrad, III
Attorney, Agent, or Firm—Townsend & Banta

[57] ABSTRACT

The present invention provides the compound containing one hydroxyl group and one acyl carbamate group per molecule, which is useful for introducing the acyl carbamate group in chemical materials. By employing the present compound, it becomes possible to introduce the acyl carbamate group in various chemical materials other than acrylic polymers. According to the present process, the compound containing one hydroxyl group and one acyl carbamate group per molecule is provided in excellent yield with a suppressed amount of by-product.

6 Claims, 1 Drawing Sheet

FIG. 1

ACYL CARBAMATE CONTAINING A HYDROXYL GROUP AND PROCESS FOR PRODUCING THE SAME

FIELD OF THE INVENTION

The present invention relates to acyl carbamate containing a hydroxyl group, that is, a compound containing one hydroxyl group and one acyl carbamate group per molecule, and to a process for producing the same.

PRIOR ART

An acyl carbamate group has been known to have high reactivity in comparison to a usual ester group. For example, it reacts with a hydroxyl group even in the absence of a catalyst. Then, if such an acyl carbamate group is introduced in various chemical materials such as polymers, development of high functional paints and high functional adhesives becomes realistic. In order to introduce the acyl carbamate group in various chemical materials, it has been desired a compound which contains an acyl carbamate group and an active hydrogen-containing functional group (particularly, a hydroxyl group) in the same molecule.

Japanese Laid-Open Patent Publication No. 61-1653 discloses a process for producing polyacylurethane comprising a step of reacting N-alkoxycarbonyl cyclic imide with polyol. The resulting polyacylurethane contains a lot of acyl carbamate groups which pendent through the hydroxyl groups from a main chain of the polyol.

The gazette also discloses a process for producing polyacyl urethane having the hydroxyl group by leaving a part of the hydroxyl group of polyol. But, the resulting polymer has large equivalent weight and is not suitable for introducing in various chemical materials.

Further, when diol is employed as polyol for this process in order to decrease the equivalent weight of the resulting polyacyl urethane, it is provided a large amount of by-product having two terminal acyl carbamate groups which was derived from the hydroxyl groups of diol. The objective compound containing one acyl carbamate group and one hydroxyl group per molecule, therefore, can scarcely be obtained according to the disclosed process.

SUMMARY OF THE INVENTION

The present invention provides the compound containing one hydroxyl group and one acyl carbamate group per molecule, which is useful for introducing the acyl carbamate group in chemical materials. By employing the present compound, it becomes possible to introduce the acyl carbamate group in various chemical materials other than acrylic polymers. According to the present process, the compound containing one hydroxyl group and one acyl carbamate group per molecule is provided in excellent yield with a suppressed amount of by-product.

DETAILED DESCRIPTION OF THE INVENTION

The present invention provides acyl carbamate of the formula:

wherein $R^1$ represents an alkylene group having up to 12 carbon atoms, which may contain an alicyclic group, an aromatic ring and/or an oxygen atom; $R^2$ represents an alkylene, arylene or alkenylene group having up to 8 carbon atoms; and $R^3$ represents an alkyl or aryl group having up to 18 carbon atoms, which may contain an oxygen atom.

In preferred embodiment of the present invention, $R^1$ is a residue of diol. The wording "residue of diol" used herein means a divalent group which is left when two hydroxyl groups of diol are eliminated. Diol employed in the present invention is not specifically limited, and include those of which residue is an alkylene group having 2 to 12, preferably 2 to 9, more preferably 2 to 6 carbon atoms, which may contain an alicyclic group, an aromatic ring and/or an oxygen atom.

Preferred examples of the diol include alkanediols such as ethylene glycol, 1,2-propylene glycol, 1,3-propylene glycol, 1,3-butanediol, 1,4-butanediol, 1,4-pentanediol, 1,5-pentanediol, neopentyl glycol, 1,6-hexanediol, 1,9-nonanediol, 1,10-decanediol, 1,12-dodecanediol, 1,2-octadecanediol, 1,8-octadecanediol, 2,5-dimethyl-2,5-hexanediol, 2,2-dimethyl-1,3-propanediol and 2,5-diethyl-2,5-hexanediol; alkenediols such as 2-butenediol and 3-hexenediol; ether bond-containing diols such as diethylene glycol and triethylene glycol; ester group-containing diols such as dihydroxyethyl carbonate; alicyclic group-containing diols such as 1,2-cyclohexanediol, 1,3-cyclohexanediol, 1,4-cyclohexanediol, 1,2-cyclopentanediol, 1,2-cyclooctanediol, 1,4-cyclooctanediol, 1,5-cyclooctenediol and 4,4-dicyclohexanediol; and aryl group-containing diols such as dibenzyl alcohol and xylylene glycol.

In the present invention, $R^2$ preferably represents a divalent hydrocarbon group such as an alkylene group, an arylene group, an alkenylene group and the like. $R^2$ has 1 to 8, preferably 2 to 6, more preferably 2 carbon atoms. In the present invention, particularly preferred examples of $R^2$ include an ethylene group, a 1,2-phenylene group, a 1,2-cyclohexylene group and an ethynyl group.

In the present invention, $R^3$ preferably represents an alkyl or aryl group which may contain oxygen. $R^3$ has 1 to 18, preferably 2 to 8, more preferably 2 to 6 carbon atoms.

Examples of $R^3$ include hydrocarbon groups such as a methyl group, an ethyl group, a n-propyl group, an isopropyl group, a n-butyl group, an isobutyl group, a t-butyl group, an amyl group, a hexyl group, a cyclohexyl group, an octyl group, a 2-ethylhexyl group, a nonyl group, a decanyl group, a stearyl group, a benzyl group, an allyl group, a propargyl group and a phenyl group; a methoxyethyl group, an ethoxyethyl group, a butoxyethyl group, a hexyloxyethyl group, a methoxyethyloxy group, an ethoxyethyloxy group, methoxypropyloxy group and a butoxyethyloxyethyl group.

Non-limiting examples of the present acyl carbamate containing a hydroxyl group is shown in the following Tables 1 to 3.

TABLE 1

| Structure | Name |
|---|---|
| HO—(CH₂)₂—O—C(=O)—C₆H₄—C(=O)—NH—C(=O)—OEt | Ethyl N-{2-(2-hydroxy-ethoxycarbonyl)benzoyl}carbamate |
| HO—(CH₂)₄—O—C(=O)—C₆H₄—C(=O)—NH—C(=O)—OEt | Ethyl N-{2-(4-hydroxy-butoxycarbonyl)benzoyl}carbamate |
| HO—(CH₂)₆—O—C(=O)—C₆H₄—C(=O)—NH—C(=O)—OEt | Ethyl N-{2-(6-hydroxy-hexyloxycarbonyl)benzoyl}-carbamate |
| HO—(CH₂)₉—O—C(=O)—C₆H₄—C(=O)—NH—C(=O)—OEt | Ethyl N-{2-(9-hydroxy-nonyloxycarbonyl)benzoyl}-carbamate |
| HO—(CH₂)₁₂—O—C(=O)—C₆H₄—C(=O)—NH—C(=O)—OEt | Ethyl N-{2-(12-hydroxy-dodecyloxycarbonyl)benzoyl}-carbamate |

TABLE 2

| Structure | Name |
|---|---|
| HOH₂C—C₆H₄—CH₂O—C(=O)—C₆H₄—C(=O)—NH—C(=O)—OEt | Ethyl N-[2-{(4-hydroxymethyl-benzyloxycarbonyl)benzoyl}]-carbamate |
| HO—C₆H₁₀—O—C(=O)—C₆H₄—C(=O)—NH—C(=O)—OEt | Ethyl N-{2-(4-hydroxy-cyclohexyloxycarbonyl)benzoyl}-carbamate |
| HO—CH₂—C(CH₃)₂—CH₂—O—C(=O)—C₆H₄—C(=O)—NH—C(=O)—OEt | Ethyl N-{2-(3-hydroxy-2,2-dimethyl-propyloxycarbonyl)benzoyl}-carbamate |

TABLE 2-continued

| Structure | Name |
|---|---|
| HO—CH₂CH₂—O—CH₂CH₂—O—CH₂CH₂—O—C(=O)—C₆H₄—C(=O)—N(H)—C(=O)—OEt | Ethyl N-{2-(8-hydroxy-3,6-dioxa-octyloxycarbonyl)benzoyl}-carbamate |
| HO—(CH₂)₆—O—C(=O)—C₆H₄—C(=O)—N(H)—C(=O)—OPh | Phenyl N-{2-(6-hydroxy-hexyloxycarbonyl)benzoyl}-carbamate |

TABLE 3

| Structure | Name |
|---|---|
| HO—(CH₂)₂—O—C(=O)—CH₂CH₂—C(=O)—N(H)—C(=O)—OEt | Ethyl N-{3-(2-hydroxy-ethoxycarbonyl)propionyl}carbamate |
| HO—(CH₂)₆—O—C(=O)—CH₂CH₂—C(=O)—N(H)—C(=O)—OEt | Ethyl N-{3-(4-hydroxy-hexyloxycarbonyl)propionyl}carbamate |
| HO—(CH₂)₆—O—C(=O)—CH₂CH₂—C(=O)—N(H)—C(=O)—O(CH₂)₂O(CH₂)₃CH₃ | Butoxyethyl N-{3-(6-hydroxy-hexyloxycarbonyl)propionyl}carbamate |
| HO—(CH₂)₆—O—C(=O)—CH=CH—C(=O)—N(H)—C(=O)—O—CH₂CH(Et)(CH₂)₃CH₃ | 2-Ethylhexyl N-{3-(6-hydroxy-hexyloxycarbonyl)propenoyl}carbamate |

Acyl carbamate containing a hydroxyl group of the present invention is prepared by reacting N-alkoxycarbonyl cyclic imide of the formula:

wherein $R^2$ and $R^3$ is the same as defined above; with the above-described diol of the formula:

HO-R¹m-OH wherein $R^1$ is the same as defined above; in an equivalent weight ratio of diol/imide more than 3. The reaction scheme is shown below.

BASIC SCHEME OF REACTION

HO−R¹−OCOR²CONHCOO−R³

Non-limiting examples of the N-alkoxycarbonyl cyclic imide which can be employed in the process of the present invention are shown in the following Table 4.

TABLE 4

| Structure | Name |
|---|---|
| Phthalimide-N-C(=O)-OEt | N-Ethoxycarbonylphthalimide |
| Phthalimide-N-C(=O)-OPh | N-Phenoxycarbonylphthalimide |
| Succinimide-N-C(=O)-OEt | N-Ethoxycarbonylsuccinimide |
| Succinimide-N-C(=O)-O(CH$_2$)$_2$O(CH$_2$)$_3$CH$_3$ | N-(2-Butoxy)ethyloxycarbonylsuccinimide |
| Maleimide-N-C(=O)-OCH$_2$CH(Et)CH$_2$CH$_2$CH$_2$CH$_3$ | N-(2-Ethylhexyloxycarbonyl)maleimide |

N-alkoxycarbonyl cyclic imides can generally be obtained by reacting cyclic imide with chloroformate according to the procedure well known to those skilled in the art.

In the process of the present invention, diol and N-alkoxycarbonyl cyclic imide is preferably reacted in an equivalent weight ratio that the hydroxyl group of diol may be 3 to 8 times, preferably 5 to 8 times based on the cyclic imide group of N-alkoxycarbonyl cyclic imide. When the equivalent weight ratio of diol to N-alkoxycarbonyl cyclic imide is less than 3, it is produced the by-product which has two terminal acyl carbamate groups both of which are converted from the hydroxyl groups of diol (diacyl carbamate), in larger amount than the objective acyl carbamate containing a hydroxyl group (monoacyl carbamate), and therefore, yield of the objective compound becomes poor.

On the other hand, when the equivalent weight ratio is more than 8, the by-product having two terminal acyl carbamate groups is scarcely produced but yield of the objective compound may not be remarkably increased.

In order to increase a reaction rate of N-alkoxycarbonyl cyclic imide and diol, it is preferred to employ a catalyst in the process of the present invention. A basic catalyst is preferred. Particularly, tertiary amine, alkali metal and the like are preferred. Examples of tertiary amine include triethylamine, tributylamine, pyridine, dimethylaminopyridine, N-methylmorpholine, N-methylpiperidine, diazabicyclo-[2,2,2]-octane and the like. Examples of alkali metal include sodium methoxide, sodium ethoxide, potassium t-butoxide and the like. An amount of the catalyst is 0.05 to 15 mol. %, preferably 0.5 to 5 mol. % based on N-alkoxycarbonyl cyclic imide.

A solvent can optionally be employed. Preferred solvents are those containing no active hydrogen, for example, hydrocarbons such as heptane, benzene, toluene and xylene; halogenated hydrocarbons such as dichloroethane and o-dichlorobenzene; esters such as butyl acetate and ethyl acetate; ketones such as methyl ethyl ketone and cyclohexanone; ethers such as dioxane and tetrahydrofuran; and aprotic solvents such as dimethyl sulfoxide and dimethylformamide.

The reaction according to the present process is generally conducted under heating. The reaction temperature employed is not specifically limited, but is preferably not more than 120° C. Excessive heating of not less than 150° C. is not preferred, because it may cause side reactions.

The following explains fundamental procedure according to the present invention. N-alkoxycarbonyl cyclic imide and diol are charged in a reaction vessel, and optionally, a catalyst and/or a solvent are added. The content is heated to a predetermined temperature and stirred. The reaction is generally completed after the lapse of predetermined time, but it can also be completed after confirming that the raw material has disappeared by usual analytical means, such as gas chromatography, liquid chromatography, thin-layer chromatography and the like.

9

The reaction mixture is treated according to usual method and may optionally be purified by using recrystallization and silica gel column chromatography to obtain an objective product. The resulting compound can be identified by measuring infrared absorption spectrum (IR), nuclear magnetic resonance spectrum (NMR) and the like.

EXAMPLES

The following Examples further illustrate the present invention in detail but are not to be construed to limit the scope thereof.

Example 1

A magnetic stirrer was placed in a reaction vessel equipped with a cooling tube and a nitrogen inlet tube, and to which were added 20.2 g (91.3 mmol) of N-ethoxycarbonylphthalimide, 57.0 g (913 mmol) of ethylene glycol and 0.4 g of triethylamine. The content was heated to 85° C. for 2.5 hours and the reaction was completed after when N-ethoxycarbonylphthalimide has disappeared, which was confirmed by thin-layer chromatography. The resulting reaction mixture was concentrated by a rotary evaporator, diluted with methylene chloride, and washed with water three times. The organic phase was dried over magnesium sulfate and the solvent was distilled off by the rotary evaporator to give 14.9 g of light yellow liquid.

Characteristics of the resulting compound was defined using the following instruments.

Melting point: MP-51965 manufactured by Yanako Co., Ltd.

Viscosity: Viscometer, Model EL, EM or EL (20° C.) manufactured by Tokyo Keiki Co., Ltd.

IR: Model FT/IR-5300 manufactured by Japan Spectroscopic CO., LTD.

NMR: ASPECT-3000 manufactured by Bruker Co., Ltd.

The resulting compound is identified as ethyl N-{2-(2-hydroxyethoxycarbonyl)benzoyl}carbamate. Structure of the resulting compound are shown in Table 5. The Field based on N-ethoxycarbonylphthalimide was 86%.

Example 2

According to the same manner as described in Example 1 except for reacting N-ethoxycarbonylphthalimide with 1,4-butanediol under conditions shown in Table 19, ethyl N-{2-(4-hydroxybutoxycarbonyl)benzoyl)carbamate was obtained. Characteristics and identified structure of the resulting compound are shown in Table 6.

Example 3

According to the same manner as described in Example 1 except for reacting N-ethoxycarbonylphthalimide with 1,6-hexanediol under conditions shown in Table 19, ethyl N-{2-(6-hydroxyhexyloxycarbonyl)benzoyl)carbamate was obtained. Characteristics and identified structure of the resulting compound are shown in Table 7.

Example 4

According to the same manner as described in Example 1 except for reacting N-ethoxycarbonylphthalimide with 1,9-nonanediol under conditions shown in Table 19, ethyl N-{2-(9-hydroxynonyloxycarbonyl)benzoyl)carbamate was obtained. Characteristics and identified structure of the resulting compound are shown in Table 8.

10

Example 5

According to the same manner as described in Example 1 except for reacting N-ethoxycarbonylphthalimide with 1,12-dodecanediol under conditions shown in Table 19, ethyl N-{2-(12-hydroxydodecyloxycarbonyl)benzoyl)carbamate was obtained. Characteristics and identified structure of the resulting compound are shown in Table 9.

Example 6

According to the same manner as described in Example 1 except for reacting N-ethoxycarbonylphthalimide with 1,4-cyclohexanediol under conditions shown in Table 19, ethyl N-{2-(4-hydroxycyclohexyloxycarbonyl-)benzoyl)carbamate was obtained. Characteristics and identified structure of the resulting compound are shown in Table 10.

Example 7

According to the same manner as described in Example 1 except for reacting N-ethoxycarbonylphthalimide with xylylene glycol under conditions shown in Table 19, ethyl N[2-{(4-hydroxymethylbenzyloxycarbonyl)benzoyl)]carbamate was obtained. Characteristics and identified structure of the resulting compound are shown in Table 11.

Example 8

According to the same manner as described in Example 1 except for reacting N-ethoxycarbonylphthalimide with neopentyl glycol under conditions shown in Table 20, ethyl N-{2-(3-hydroxy-2,2-dimethylpropyloxycarbonyl)benzoyl)carbamate was obtained. Characteristics and identified structure of the resulting compound are shown in Table 12.

Example 9

According to the same manner as described in Example 1 except for reacting N-ethoxycarbonylphthalimide with triethylene glycol under conditions shown in Table 20, ethyl N-{2-(8-hydroxy-3,6-dioxaoctyloxycarbonyl)benzoyl-)carbamate was obtained. Characteristics and identified structure of the resulting compound are shown in Table 13.

Example 10

According to the same manner as described in Example 1 except for reacting N-phenoxycarbonylphthalimide with 1,6-hexanediol under conditions shown in Table 20, phenyl N-{2-(6-hydroxyhexyloxycarbonyl)benzoyl} carbamate was obtained. Characteristics and identified structure of the resulting compound are shown in Table 14.

Example 11

According to the same manner as described in Example 1 except for reacting N-ethoxycarbonylsuccinimide with ethylene glycol under conditions shown in Table 20, ethyl N-{ 3-(2-hydroxyethoxycarbonyl)propionyl)carbamate was obtained. Characteristics and identified structure of the resulting compound are shown in Table 15.

Example 12

According to the same manner as described in Example 1 except for reacting N-ethoxycarbonylsuccinimide with 1,6-hexanediol under conditions shown in Table 20, ethyl N-{3-(4-hydroxyhexyloxycarbonyl)propionyl)carbamate was obtained. Characteristics and identified structure of the resulting compound are shown in Table 16.

Example 13

According to the same manner as described in Example 1 except for reacting N-butoxyethyloxycarbonylsuccinimide with 1,6-hexanediol under conditions shown in Table 20, butoxyethyl N-{3-(6-hydroxyhexyloxycarbonyl)propionyl}carbamate was obtained. Characteristics and identified structure of the resulting compound are shown in Table 17.

Example 14

According to the same manner as described in Example 1 except for reacting N-(2-ethylhexyloxycarbonyl)maleimide with 1,6-hexanediol under conditions shown in Table 20, 2-Ethylhexyl N-{3-(6-hydroxyhexyloxycarbonyl)propenoyl}carbamate was obtained. Characteristics and identified structure of the resulting compound are shown in Table 18.

Example 15

N-ethoxycarbonylphthalimide and ethanediol are reacted in dioxane at 85° C. for 3.5 hours in the presence of t-butoxypotassium as a catalyst, in a variety of equivalent weight ratio of diol/imide between 1 to 5. Ethyl N-{2-(2-hydroxyethoxycarbonyl)benzoyl}carbamate (3) which is monoacyl carbamate of diol, and diacyl carbamate of diol (4) were obtained.

The resulting monoacyl carbamate (3) is the objective acyl carbamate containing a hydroxyl group, and the diacyl carbamate (4) is the by-product which has two terminal acyl carbamate groups both of which are converted from the hydroxyl groups of diol.

The respective amounts of the monoacyl carbamate (3) and diacyl carbamate (4) were then determined according to H-NMR using benzyl alcohol as a standard. The result is shown in FIG. 1.

Figure 1:
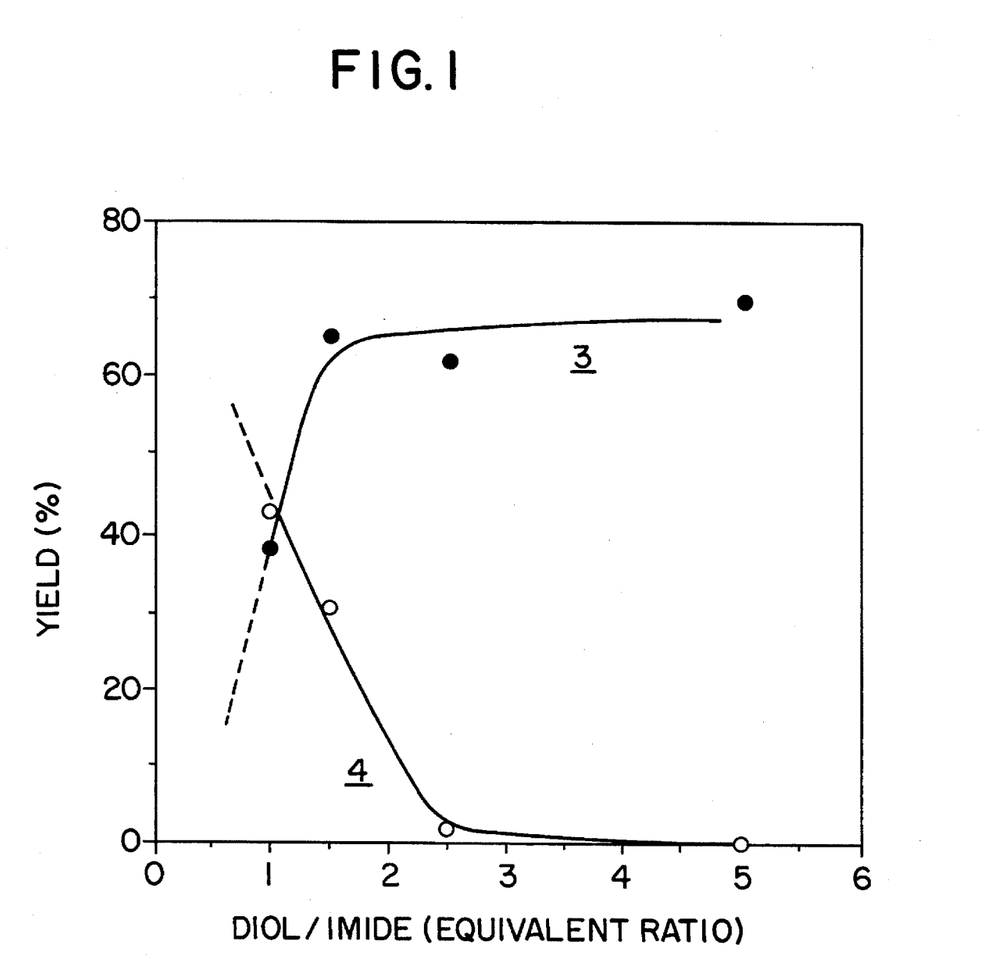
FIG. 1 is a graph illustrating a relation between yield of ethyl N-{2-(2-hydroxyethoxycarbonyl)benzoyl)carbamate (3) which is acyl carbamate containing a hydroxyl group of the present invention and equivalent weight ratio of ethylene glycol/N-ethoxycarbonylphthalimide.

As shown in FIG. 1, the present monoacyl carbamate (3) is preferentially formed when the process is conducted in an equivalent weight ratio of diol/imide not less than 3.

TABLE 5

| Formula |  |
|---|---|
| Appearance | Colorless oil |
| Viscosity(cps) (Model EH) | $2.29 \times 10^4$ |
| $^1$H-NMR (360MHz, CDCl$_3$) | δ; 1.26(t, 3H, Et), 3.38(t, 2H, HOCH$_2$CH$_2$), 4.16(q, 2H, Et), 4.43(t, 2H, HOCH$_2$CH$_2$) 7.38(d, 1H, Ph), 7.52–7.64(m, 2H, Ph), 8.05(d, 1H, Ph), 8.23(br, 1H, NH) |
| IR(cm$^{-1}$) (KBr film) | 3450(HO), 3250(NH), 1760(CO), 1710(CO), 1280(PhCOOC), 1200(CONHCOO) |

TABLE 6

| Formula |  |
|---|---|
| Appearance | Light yellow oil |
| Viscosity(cps) (Model EH) | $9.84 \times 10^3$ |
| $^1$H-NMR (360MHz, CDCl$_3$) | δ: 1.20(t, J=7.1Hz, 3H, Et), 1.68–1.88(m, 4H, CH$_2$CHCH$_2$OCO—Ph)4.12(q, J=7.1Hz, 2h, Et), 4.34(t, J=6.3Hz, 2H, CH$_2$OCO—Ph), 7.37(m, 1H, Ph), 7.52–7.63(m, 2H, Ph), 8.08(m, 1H, Ph)8.17(br, 1H, NH) |
| IR(cm$^{-1}$) (KBr film) | 3450(OH), 3250(NH), 1760(CO), 1700(CO), 1270(PhCOOC), 1200(CONHCOO) |

TABLE 7

| Formula |  |
|---|---|
| Appearance | Light yellow oil |
| Viscosity(cps) (Model EM) | $3.58 \times 10^2$ |
| $^1$H-NMR (360MHz, CDCl$_3$) | δ; 1.20(t, J=6.8Hz, 3H, Et), 4.45(br, 4H, HO—(CH$_2$CH$_2$CH$_2$CH$_2$CH$_2$) 1.58(m, 2H, HOCH$_2$CH$_2$), 1.75(m, 2H, CH$_2$CH$_2$—OCO—Ph), 1.85(br, 1H, HO)3.67 (br, 2H, HOCH$_2$), 4.11(q, J=6.8Hz, 2H, Et), 4.30(t, J=6.4Hz, 2H, CH$_2$—OCO—Ph), 7.35(d, J=7.4Hz, 1H, Ph)7.51–7.60(m, 2H, Ph), |

TABLE 7-continued

Formula

| | |
|---|---|
| IR(cm⁻¹) (KBr film) | 8.03(d, , J=7.7Hz, 1H, Ph), 8.4(br, 1H, NH) 3450(OH), 3250(NH), 1760(CO), 1700(CO), 1290(PhCOOC), 1210(CONHCOO) |

TABLE 8

Formula

| | |
|---|---|
| Appearance | Light yellow oil |
| Viscosity(cps) (Model EM) | $3.84 \times 10$ |
| ¹H-NMR (360MHz, CDCl₃) | δ; 1.22(t, J=7.1Hz, 3H, Et), 1.32(br, 10H, HO—(CH₂CH₂(C$\underline{H}$₂)₅CH₂CH₂) 1.55(br, 2H, HOCH₂C$\underline{H}$₂), 1.73(br, 2H, C$\underline{H}$₂CH₂—OCO—Ph), 3.64(t, J=7.0Hz, 2H, HOC$\underline{H}$₂), 4.12(q, J=7.1Hz, 2H, Et), 4.29(t, J=6.7Hz, 2H, C$\underline{H}$₂—OCO—Ph), 7.35(d, 1H, Ph), 7.50–7.62(m, 2H, Ph), 8.04(d, J=7.8Hz, 1H, Ph), 8.1(br, 1H, NH) |
| IR(cm⁻¹) (KBr film) | 3450(OH), 3250( NH), 1760(CO), 1700(CO), 1270(PhCOOC), 1200(CONHCOO) |

TABLE 9

Formula

| | |
|---|---|
| Appearance | White wax |
| Viscosity(cps) (Model EH) | $13\sim1.7 \times 10^3$ |
| ¹H-NMR (360MHz, CDCl₃) | δ; 1.21(t, 3H, Et), 1.27(br, 16H, HOCH2CH2(CH2)8-), 1.56(q, 2H, HOCH2C$\underline{H}$2), 1.73(q, 2H, C$\underline{H}$2CH2OCO), 3.62(t, 2H, HOC$\underline{H}$2), 4.12(q, 2H, Et), 4.28(t, 2H, C$\underline{H}$2OCO), 7.37(d, 1H, Ph), 7.51(t, 1H, Ph), 7.58(t, 1H, Ph), 8.02(d, 1H, Ph), 8.4(br, 1H, NH) |
| IR(cm⁻¹) (KBr film) | 3400(HO), 3250(NH), 1760(CO), 1720(CO), 1700(CO), 1290(PhCOOC), 1200(CONHCOO) |

TABLE 10

Formula

| | |
|---|---|
| Appearance | Colorless semisolid oil |
| Viscosity(cps)[1) (Model EM) | $6.1 \times 10$ |
| ¹H-NMR (360MHz, CDCl₃) | δ; 1.21(t, 3H, Et), 1.39–2.16(m, 8H, Cy), 3.28(br, 1H, C$\underline{H}$—OCOPh)4.12(q, 2H, Et), 4.97+5.14(m+m, 1H, HO—C$\underline{H}$)* 7.36(d, 1H, Ph), 7.50–7.62(m, 2H, Ph), 8.05(m, 1H, Ph), 8.24+8.55(br+br, 1H, NH)* |
| IR(cm⁻¹) (KBr film) | 500(OH), 3270(NH), 1770(CO), 1720(CO), 1290(PhCOOC), 1200(CONHCOO) |

[1)]: 67% Dioxane solution
*; Cis-trans mixture

TABLE 11

| Formula | |
|---|---|
| Appearance | Light yellow oil |
| Viscosity(cps)[1] (Model EL) | 8.0 × 10 |
| $^1$H-NMR (360MHz, CDCl$_3$) | δ; 1.18(t, 3H, Et), 1.78(br, 1H, HO), 4.05(q, 2H, Et), 4.68(d, 2H, HOC$\underline{H}_2$—Ph)5.29(d, 2H, PhC$\underline{H}_2$OCOPh), 7.34–7.41(m, 5H, Ph), 7.48–7.62(m, 2H, Ph), 8.05(d, 1H, Ph), 8.0(br, 1H, NH) |
| IR(cm$^{-1}$) (KBr film) | 3450(HO), 3250(NH), 1760(CO), 1750(CO), 1260(PhCOOC), 1200(CONHCOO) |

[1]: 67% Dioxane solution

TABLE 12

| Formula | |
|---|---|
| Appearance | Colorless crystal |
| m.p.(°C.) | 109 |
| $^1$H-NMR (360MHz, CDCl$_3$) | δ; 0.97(s, 6H, CH$_3$), 1.22(t, 3H, Et), 3.35(t, 2H, HOC$\underline{H}_2$), 4.12(q, 2H, Et) 7.37(d, 2H, Ph), 7.52–7.65(m, 2H, Ph), 8.03(d, 1H, Ph), 8.21(br, 1H, NH) |
| IR(cm$^{-1}$) (KBr disk) | 3480(HO), 3230, 3150(NH), 1775(CO), 1735(CO), 1210(CONHCOO) |

TABLE 13

| Formula | |
|---|---|
| Appearance | Colorless oil |
| Viscosity(cps) (Model EH) | 3.79 × 10$^4$ |
| $^1$H-NMR (360MHz, CDCl$_3$) | δ; 1.17(t, 3H, Et), 3.53+3.71(m+m, 2H, HOC$\underline{H}_2$), 3.71(m, 4H, C$\underline{H}_2$OC$\underline{H}_2$) 3.80(m, 4H, PhCOOCH2C$\underline{H}_2$, HOCH$_2$C$\underline{H}_2$), 4.08(q, 2H, Et) 4.41+4.46(m+m, 2H, C$\underline{H}_2$OCOPh)7.34(d, 1H, Ph), 7.49–7.60(m, 2H, Ph) 8.07(m, 1H, Ph), 9.27+9.54(br+br, 1H, NH) |
| IR(cm$^{-1}$) (KBr film) | 3500(OH), 3260(NH), 1760(CO), 1725(CO), 1700(CO), 1290(PhCOOC), 1200(CONHCOO) |

TABLE 14

| Formula | |
|---|---|
| Appearance | Colorless oil |
| Viscosity(cps) (Model EH) | $7.20 \times 10^2$ |
| $^1$H-NMR (360MHz, CDCl$_3$) | δ; 1.30–1.80(m, 3H, C$\underline{H}_2$), 3.64(t, 2H, HOC$\underline{H}_2$), 4.28(t, 2H, C$\underline{H}_2$OCOPh), 6.88(m, 2H, Ph), 7.21(m, 2H, Ph), 7.35(m, 1H, Ph), 7.48(m, 1H, Ph), 7.58(m, 1H, Ph), 8.50(m, 1H, Ph), 8.50(br, 1H, NH) |
| IR(cm$^{-1}$) (KBr film) | 3450(HO), 3250(NH), 1760(CO), 1720(CO), 1280(PhCOOC), 1200(CONHCOO) |

TABLE 18

| Formula | |
|---|---|
| Appearance | Colorless oil |
| Viscosity(cps) (Model EM) | $3.10 \times 10^2$ |
| $^1$H-NMR (360MHz, CDCl$_3$) | δ; 0.90(t, 3H, C$\underline{H}_3$), 1.29–1.45(m, 10H, C$\underline{H}_2$), 1.57–1.73(m, 4H, HO—CH$_2$C$\underline{H}_2$), 2.00(br, 1H, CH$_2$C$\underline{H}$(CH$_3$)), 3.66(t, 2H, HO—C$\underline{H}_2$), 4.09(t, 2H, C$\underline{H}_2$OCOCH=CH), 4.17(q, 2H, CONHCOOC$\underline{H}_2$), 6.13(d, 1H, OCOC$\underline{H}$=CHCONHCOO), 6.70(d, 1H, OCOC$\underline{H}$=CHCONHCOO), 9.05(br, 1H, NH) |
| IR(cm$^{-1}$) (KBr film) | 3500(OH), 3250(NH), 1760(CO), 1720(CO), 1700(CO), 1200(CONHCOO) |

TABLE 15

| Formula | |
|---|---|
| Appearance | White crystal |
| m.p.(°C.) | 62 |
| $^1$H-NMR (360MHz, CDCl$_3$) | δ; 1.90(t, 3H, Et), 2.51(t, 2H, C$\underline{H}_2$COO), 2.71(t, 2H, C$\underline{H}_2$CONHCOO), 3.53(br, 2H, C$\underline{H}_2$OH), 3.99(t, 2H, C$\underline{H}_2$OCO), 4.09(q, 2H, Et), 4.77(br, 1H, $\underline{H}$OCH$_2$) |
| IR(cm$^{-1}$) (KBr film) | 3450(HO), 3250(NH), 1760(NH$\underline{C}$OOEt), 1710(CO), 1200(CONHCOO) |

TABLE 16

| Formula | |
|---|---|
| Appearance | White crystal |
| m.p.(°C.) | 78 |
| $^1$H-NMR (360MHz, CDCl$_3$) | δ; 1.31(t, 3H, Et), 1.37–1.41(br, 4H, HO—CH$_2$C$\underline{H}_2$C$\underline{H}_2$CH$_2$) 1.57(m, 2H, HOCH$_2$C$\underline{H}_2$), 1.65(m, 2H, C$\underline{H}_2$CH$_2$—OCO), 2.66(t, 2H, C$\underline{H}_2$COO), 3.08(t, 2H, C$\underline{H}_2$CONHCOO) 3.65(br, 2H, C$\underline{H}_2$OH), 4.09(t, 2H, C$\underline{H}_2$OCO), 4.22(q, 2H, Et), 7.64(br, 1H, NH), |
| IR(cm$^{-1}$) (KBr film) | 3230, 3170(NH), 1750(NHCOOEt), 1720(COO), 1200(CONHCOO) |

TABLE 17

| Formula | |
|---|---|
| Appearance | White crystal |
| m.p.(°C.) | 74 |
| $^1$H-NMR (360MHz, CDCl$_3$) | δ; 0.91(t, 3H, —CH$_3$), 1.38(m, 6H, —CH$_2$—), 1.54–1.74(m, 6H, —CH$_2$—), 2.66(t, 2H, —OCOC$\underline{H}_2$—), 3.08(t, 2H, —C$\underline{H}_2$CONHCOO—), 3.47(t, 2H, —OCH$_2$CH$_2$OC$\underline{H}_2$—), 3.65(t, 4H, —CONHCOOC$\underline{H}_2$+HOC$\underline{H}_2$—), 4.10(t, 2H, —NHCOOC$\underline{H}_2$—), 4.31(t, 2H, —CH$_2$CH$_2$COOC$\underline{H}_2$—), 7.76(br, 1H, NH) |
| IR(cm$^{-1}$) (KBr film) | 3270, 3200(NH), 1760(CO), 1730($\underline{C}$O), 1225(CONHCOO) |

TABLE 19

| Examples | R² | R³ | R¹ | Imide (g/mmol) | Diol (g/mmol) | Catal. (g) | Solv. (g) | Temp. (°C.) | Time (h) | Yield (%) | m.p. or Vis. | Notes |
|---|---|---|---|---|---|---|---|---|---|---|---|---|
| 1 | (o)-Ph | Et | $-C_2-$ | 20/91.3 | 57/913 | TEA (0.4) | None | 85 | 2.5 | 86 | $\eta$ (cps) = $2.29 \times 10^4$ | |
| 2 | (o)-Ph | Et | $-C_4-$ | 6.57/30 | 4.05/45 | DABCO (0.25) | Dioxane (20) | 60 | 3 | 63 | $\eta$ (cps) = $9.84 \times 10^3$ | |
| 3 | (o)-Ph | Et | $-C_6-$ | 50/228 | 90/761 | DABCO (2.5) | Dioxane (100) | 60 | 3 | 69 | $\eta$ (cps) = $3.58 \times 10^2$ | |
| 4 | (o)-Ph | Et | $-C_9-$ | 6.57/30 | 7.20/45 | DABCO (0.25) | Dioxane (20) | 60 | 3 | 67 | $\eta$ (cps) = $3.84 \times 10^2$ | |
| 5 | (o)-Ph | Et | $-C_{12}-$ | 4.38/20 | 8.09/40 | DABCO (0.25) | Dioxane (20) | 65→80 | 3→1.5 | 85 | $\eta$ (cps) = $1.3 \times 10^4$ | |
| 6 | (o)-Ph | Et | ‐⟨H⟩‐ | 6.57/30 | 6.97/60 | DABCO (0.25) | Dioxane (20) | 60→80 | 3.5→1.5 | 80 | $\eta$ (cps) = $6.1 \times 10^*$ | Cis-trans mixture isolated by column chromatography |
| 7 | (o)-Ph | Et | $-H_2C-$⟨⟩$-CH_2-$ | 6.57/30 | 8.28/60 | DABCO (0.25) | Dioxane (20) | 60 | 3.5 | 66 | $\eta$ (cps) = $8.0 \times 10^*$ | |

TEA = Triethylamine, DABCO = Diazabicyclo[2,2,2]octane, * = 67% Dioxane solution, ** = 70% Dioxane solution

TABLE 20

| Examples | $R^2$ | $R^3$ | $R^1$ | 1 (g/mmol) | 2 (g/mmol) | Catal. (g) |
|---|---|---|---|---|---|---|
| 8 | (o)-Ph | Et |  | 6.57/30 | 6.24/60 | DABCO (0.25) |
| 9 | (o)-Ph | Et |  | 4.38/20 | 6.01/40 | DABCO (0.25) |
| 10 | (o)-Ph | Ph | $-C_6-$ | 1.0/3.75 | 0.89/7.5 | DABCO (0.02) |
| 11 | $CH_2CH_2$ | Et | $-C_2-$ | 20/117 | 8.7/140 | TEA (0.50) |
| 12 | $CH_2CH_2$ | Et | $-C_6-$ | 20/117 | 55.2/467 | DABCO (0.13) |
| 13 | $CH_2CH_2$ |  o-n-Bu | $-C_6-$ | 4.86/20 | 4.73/40 | DABCO (0.17) |
| 14 | $-CH=CH-$ |  | $-C_6-$ | 1.0/3.95 | 0.93/7.9 | DABCO (0.20) |

| Examples | Solv. (g) | Temp. (°C.) | Time (h) | Yield (%) | m.p. or Vis. | Notes |
|---|---|---|---|---|---|---|
| 8 | Dioxane (20) | 60 | 4 | 78 | mp = 109° C. | Recrystallization[1] |
| 9 | Dioxane (20) | 65 | 3 | 65 | η (cps) = 3.79 × 10$^4$ | |
| 10 | Dioxane (4) | 60 | 5 minutes | 41 | η (cps) = 7.2 × 10$^2$ | |
| 11 | Dioxane (30) | 90 | 2.5 | 45 | mp = 62 3° C. | Recrystallization[1] |
| 12 | Dioxane (100) | 65 | 3 | 51 | mp = 82° C. | Recrystallization[2] |
| 13 | Dioxane (20) | 65→85 | 3.5→1.5 | 60 | mp = 72° C. | Recrystallization[1] |
| 14 | Dioxane (4) | 30 | 5 | 67 | η (cps) = 3.1 × 10$^2$ | |

TEA = Triethylamine, DABCO = Diazabicyclo[2,2,2]octane, [1] = Ethyl acetate/Hexane, [2] Toluene

What is claimed is:

1. An acyl carbamate of the formula:

$$HO-R^1-\underset{\underset{O}{\|}}{O}C-R^2-\underset{\underset{O}{\|}}{C}\underset{\underset{O}{\|}}{N}COR^3$$
$$\phantom{HO-R^1-OC-R^2-C}H$$

wherein $R^1$ represents an alkylene group having up to 12 carbon atoms, which may contain an alicyclic group, an aromatic ring and/or an oxygen atom; $R^2$ represents an alkylene, arylene or alkenylene group having up to 8 carbon atoms; and $R^3$ represents an alkyl or aryl group having up to 18 carbon atoms, which may contain an oxygen atom.

2. The acyl carbamate according to claim 1, wherein $R^1$ is a residue of diol.

3. The acyl carbamate according to claim 2, wherein the diol is selected from the group consisting of alkanediols, alkenediols, ether bond-containing diols, ester group-containing diols, alicyclic group-containing diols and aryl group-containing diols.

4. The acyl carbamate according to claim 2, wherein the diol is selected from the group consisting of ethylene glycol, 1,2-propylene glycol, 1,3-propylene glycol, 1,3-butanediol, 1,4-butanediol, 1,4-pentanediol, 1,5-pentanediol, neopentyl glycol, 1,6-hexanediol, 1,9-nonanediol, 1,10-decanediol, 1,12-dodecanediol, 1,2-octadecanediol, 1,8-octadecanediol, 2,5-dimethyl-2,5-hexanediol, 2,2-dimethyl-1,3-propanediol, 2,5-diethyl-2,5-hexenediol, 2-butenediol, 3-hexenediol, diethylene glycol, triethylene glycol, dihydroxyethyl carbonate, 1,2-cyclohexanediol, 1,3-cyclohexanediol, 1,4-cyclohexanediol, 1,2-cyclopentanediol, 1,2-cyclooctanediol, 1,4-cyclooctanediol, 1,5-cyclooctenediol, 4,4'-dicyclohexanediol, 1,2-benzene dimethanol, dibenzyl alcohol and xylylene glycol.

5. The acyl carbamate according to claim 1, wherein $R^2$ is selected from the group consisting of an ethylene group, a 1,2-phenylene group, a 1,2-cyclohexylene group and an ethynyl group.

6. The acyl carbamate according to claim 1, wherein $R^3$ is selected from the group consisting of a methyl group, an ethyl group, a n-propyl group, an isopropyl group, a n-butyl group, an isobutyl group, a t-butyl group, an amyl group, a hexyl group, a cyclohexyl group, an octyl group, a 2-ethylhexyl group, a nonyl group, a decanyl group, a stearyl group, a benzyl group, an allyl group, a propargyl group, a phenyl group, a methoxyethyl group, an ethoxyethyl group, a butoxyethyl group, a hexyloxyethyl group, a methoxyethyloxy group, an ethoxyethyloxy group, a methoxypropyloxy group and a butoxyethyloxyethyl group.

* * * * *